United States Patent [19]

Bauer et al.

[11] 4,036,952
[45] July 19, 1977

[54] ETHYLENEIMINE INACTIVATED MICROORGANISMS

[75] Inventors: Kurt Bauer; Günther Wittmann; Manfred Mussgay, all of Tuebingen; Eckart Irion, Wuppertal; Horst Geilhausen, Bensberg, all of Germany

[73] Assignee: Bayer Aktiengesellschaft, Germany

[21] Appl. No.: 617,038

[22] Filed: Sept. 26, 1975

Related U.S. Application Data

[60] Continuation-in-part of Ser. No. 559,970, March 19, 1975, abandoned, which is a division of Ser. No. 444,483, Feb. 21, 1974, abandoned.

[30] Foreign Application Priority Data

Feb. 24, 1973  Germany .................... 2309329

[51] Int. Cl.$^2$ ............................... A61K 39/12
[52] U.S. Cl. ................................. 424/89; 195/1.4
[58] Field of Search ............... 424/89, 244; 195/1.4

[56] References Cited

U.S. PATENT DOCUMENTS

| | | | |
|---|---|---|---|
| 3,318,775 | 5/1967 | Melvin et al. | 424/89 |
| 3,636,196 | 1/1972 | Bauer et al. | 424/89 |

OTHER PUBLICATIONS

Walpole et al., Brit. J. Pharmacol g: 306–323 (1954) "The Carcinogenic Actions of Some Monofunctional Ethyleneimine Derivatives".
Brown et al., Chem. Abst. 60, No. 6064c (1964) abst. of "The Use of Acetylethylenimine in the Production of Inactivated Foot-and-Mouth Disease Vaccines "J. Hyg. 61: 337–344, (1963).
Phillips, C. R., Chem. Abst. 70, No. 40617h (1969) abst. of "Gaseous Sterilization" U.S. Clearinghouse Fed. Sci. Tech. Inform, (1968), ad-671373, p. 17.
Bauer, K., Chem. Abst. 73, No. 32703e (1970) abst. of "Inactivation of Foot and Mouth Disease Virus by Ethylethylenimine and the Use of the Inactivated Virus in the Preparation of Vaccines" Zentralbl. Bakteriol. Parasitonk. Infektion Skr. Hyg. Abt. 1: Orig (1970) 213(3): 285–297.
Hoffman, R. K., "Toxic Gases" Chap. 4, pp. 254–255, "Inhibition and Destruction of the Microbial Cell" Hugo, Ed., Academic Press, N.Y. (1971).
Vorontsova, T. V., Chem. Abst. 76, No. 539b (1972) abst. of "Induction of S–Mutation in Fowl Plague Virus by Ethylenimine" Vop. Virusol. (1971), 16(4): pp. 416–421.
Cunliffe, H. R., Applied Microbiology 26(5): 747–750, Nov. 1973, "Inactivation of Foot-and-Mouth Disease Virus with Ethylenimine".
Warrington, R. E. et al., Am. J. Vet. Res. 34(8): 1087–1091, Aug. 1973, "Derivatives of Aziridine as Inactivants for Foot-and-Mouth Disease Virus Vaccines".

*Primary Examiner*—Shep K. Rose

[57] ABSTRACT

Microorganisms can be rendered inactive without impairing their antigenicity or immunogenicity by treating the microorganisms with ethyleneimine. The microorganism is placed in a suspension containing ethyleneimine up to a final concentration of 0.005% to 2% V/V. The temperature of the ethyleneimine-containing suspension is maintained between 0° C and 45° C for between a few hours and 2 days. The excess ethyleneimine is destroyed.

31 Claims, 1 Drawing Figure

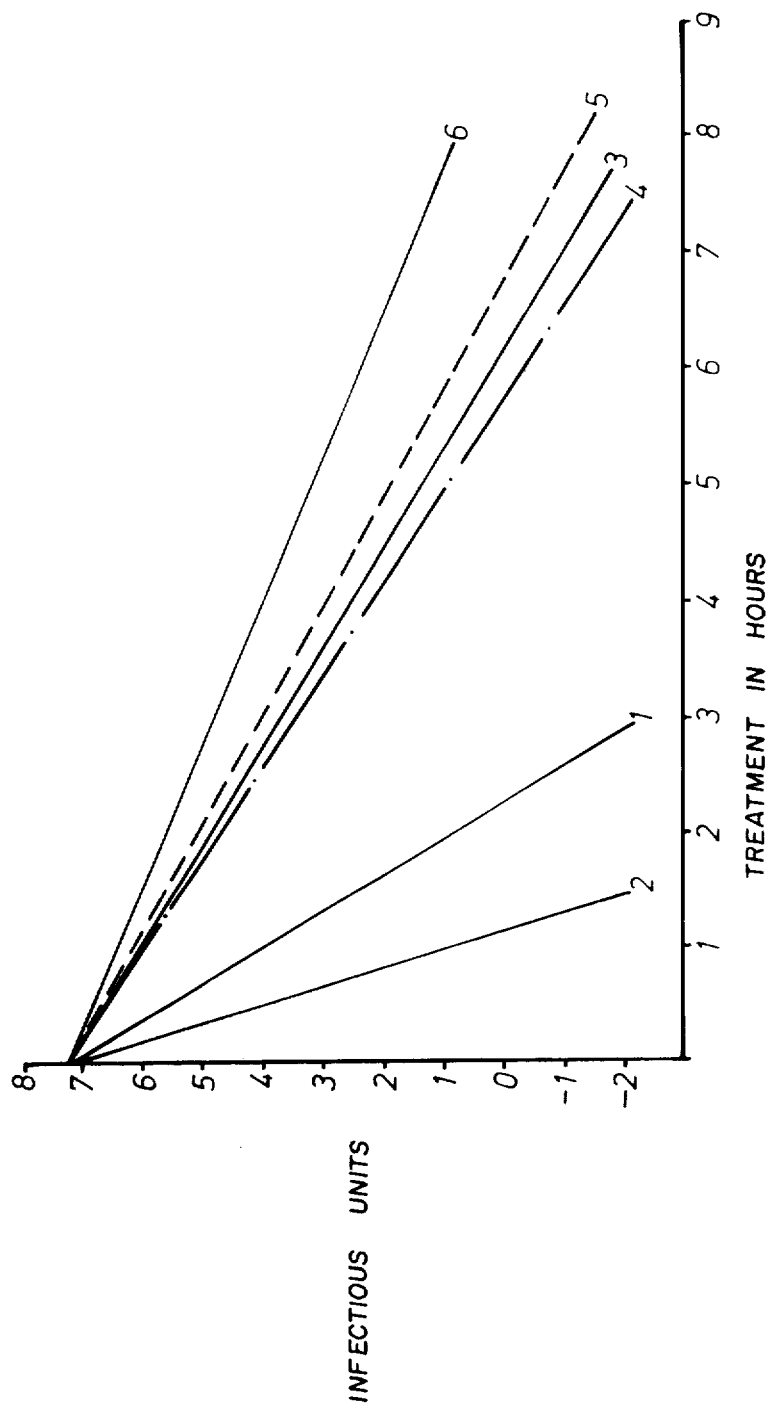

ETHYLENEIMINE INACTIVATED MICROORGANISMS

This is a continuation-in-part of our copending application Ser. No. 559,970 filed Mar. 19, 1975, which is a division of Ser. No. 444,483 Feb. 21, 1974, both now abandoned.

The present invention is concerned with the use of ethyleneimine as an inactivator in the production of immunizing substances such as antigens or immunogens. Ethyleneimine per se is a known compound. Various methods of microorganism inactivation are known in the art.

For the production of various pharmaceutical preparations as for instance inactivated virus and bacterial vaccines, it is necessary to use inactivators which on the one hand destroy the infectiousness of the used viruses or bacteria, but, on the other hand, leave the antigenic properties wholly in tact. However, in order to obtain reliably and consistently inactivated virus or bacteria preparations, the process must take place in a first-order reaction so that the point in time of complete loss of the infectiousness can be determined reliably and consistently. This is not the case with various known methods of inactivation such as heat or ultraviolet light or the use of inactivators such as formaldehyde, hydrogen peroxide or $\beta$-propiolactone. Other known substances which do not possess those disadvantages are chemically rather unstable, such as, for example, the acylethyleleimines (DBP No. 1,041,648), or they require a longer period of action and/or higher concentrations, such as, for example, ethylethyleneimine, U.S. Pat. No. 3,636,196.

The present invention comprises the use of ethyleneimine which has the formula $$\begin{array}{c} CH_2 \\ | \quad \diagdown \\ \quad \quad N-H \\ | \quad \diagup \\ CH_2 \end{array}$$

as an inactivator in the manufacture of immunizing substances such as antigens or immunogens. More particularly, the present invention relates to a method of rendering a microorganism inactive without impairing its antigenicity or immunogenicity which comprises adding to a microorganism suspension ethyleneimine at to a final concentration of 0.005% to 2% V/V and maintaining the temperature of the ethyleneimine-containing suspension between 0° C and 45° C for between a few hours and 2 days.

The excess ethyleneimine is destroyed in any suitable manner. One suitable manner is to use an agent such as sodium thiosulphate or sodium sulphite or an agent of the formula HY wherein Y is hydroxy, O alkyl, preferably O lower alkyl, NH alkyl preferably NH lower alkyl, O aryl preferably monoaryl such as phenyl, S alkyl preferably S lower alkyl or COO alkyl preferably COO lower alkyl. The amount of agent is not critical. A convenient amount is a 2% concentration, i.e., 10% by volume of a 20% strength solution, but other convenient amounts can be used.

When Y is hydroxy, the agent is, of course, water. Excess ethyleneimine is destroyed in aqueous solution without adding any agent. For example, at a temperature of 37° C, 30% of the excess ethyleneimine is destroyed after 12 hours. Thus, a further suitable manner for destroying the excess ethyleneimine is to allow an aqueous suspension of ethyleneimine and microorganism to stand at a suitable temperature for a period of time sufficient to destroy the excess ethyleneimine. 37° C for about 16 to 20 hours are suitable conditions.

When the microorganism is FMD virus, the pH should be kept in the range of 7 to 9.

The microorganism obtained according to the above process has been rendered inactive without impairing its antigenicity or immunogenicity. The thus-treated microorganism may be used according to techniques per se known for treatment and/or prophylaxis of bacterial and viral infections and can either be administered as such or may be combined into suitable pharmaceutical preparations according to techniques which are themselves per se known.

The use of ethyleneimine as an inactivator as above described does not exhibit the disadvantages of previously-known inactivators. Ethyleneimine is very easily obtainable, is quite stable, can be stored easily and permits a rapid and reliable inactivation of the microorganism in a first-order reaction without impairing the antigenicity or immunogenicity of the microorganism. As a result of the short reaction time at comparatively low concentrations, i.e., 0.005% to 2% V/V, the inactivation takes place under conditions which are extremely mild with respect to the microorganism to be inactivated.

According to one embodiment of the present invention, the microorganism is a virus such as, for example FMD Type C, and FMD Type $O_1$ or IBR. According to another embodiment of the present invention the microorganism is a bacteria such as, for example, *Pasteurella haemolitica*.

According to another embodiment of the present invention, the final concentration of ethyleneimine is from 0.01% to 0.5% V/V.

The virus strains and bacteria strains inactivated according to the present invention can be administered to humans and animals orally or parenterally according to techniques per se known. The techniques for formulating the inactivated virus or bacterial antigens obtained according to the present invention include, for example, diluting the virus preparation or bacterial preparation with suitable solvents and/or diluents or carriers according to techniques which are well known in the pharmaceutical art and administering such to a human or animal in need thereof. Thus, according to another embodiment of the present invention, a therapeutically effective amount of an inactivated bacteria or virus suspension of the present invention is combined with a pharmaceutically acceptable, nontoxic, inert diluent or carrier. Oral, intramuscular, intraperitoneal, subcutaneous and topical application are the customary routes of utilization of the inactivated virus or bacteria.

The following nonlimitative examples more particularly illustrate the present invention and demonstrate the use of a representative inactivated virus in baby mice.

EXAMPLE 1

A 2% strength (volume/volume) neutralized solution of ethyleneimine was added up to a final concentration of 0.03% (volume/volume) to a solution of Foot and Mouth Disease (FMD) virus, type C, pH 8.0, in the form of the centrifuged culture liquid from an infected culture of permanent calves' testes cells. The mixture was kept at 37° C while stirring. After certain times, samples thereof were taken. The inactivation reaction was stopped and the excess ethyleneimine destroyed in each case by adding 10% by volume of a 20% strength sodium thiosulphate solution. The samples withdrawn were then inoculated, undiluted and diluted by factors of 10, in amounts of 0.1 ml onto groups of 10 tissue culture test tubes containing primary calves' kidney cells. The virus strengths thereby determined showed a decrease with time which corresponded to a first-order reaction. After a period of treatment of 3 hours, infectiousness was no longer detectable even if 0.5 ml were inoculated. The figure shows the course of the inactivation of FMD virus, type C, at 37° C and pH 8.0. The logarithm of the infectious units is plotted on the ordinate and the period of treatment in hours is plotted on the abscissa. Curve 1 shows the course of the inactivation at a final concentration of 0.03% (volume/volume).

A virus solution treated in this way for 4 hours was inoculated intraperitoneally in an amount of 0.1 ml to 20 baby mice which were 3 to 4 days old and inoculated subcutaneously in an amount of 1.5 ml to 5 guinea pigs. None of the animals showed any disease symptoms. Three weeks after the inoculation, neutralizing antibodies against the infectious starting virus which had not been pretreated were detectable in the serum of all the guinea pigs.

The virus solution inactivated in this way showed an equally high complement fixation capacity as the untreated active virus starting solution.

EXAMPLE 2

In accordance with the process described in Example 1, the following substances and concentrations were employed instead of 0.03% (volume/volume) of ethyleneimine:

a. 0.05% (volume/volume) of ethyleneimine (See FIGURE, Curve 2)
b. 0.05% (volume/volume) of ethylethyleneimine (See FIGURE, Curve 3)
c. 0.05% (volume/volume) of N-acetylethyleneimine (See FIGURE, Curve 4)
d. 0.05% (volume/volume) of 2,2'-dimethylethyleneimine (See FIGURE, Curve 5)
e. 0.05% (volume/volume) of isopropylethyleneimine (See FIGURE, Curve 6)

The FIGURE shows the course of the inactivation. In the case of ethyleneimine (Curve 2), infectious virus was no longer detectable after 1.5 hours, while with the remaining substances this state was only reached after 7 to 8 hours or 11 hours.

EXAMPLE 3

The process described in Example 1 was repeated at a reaction temperature of 22° C instead of 37° C. The infectiousness again decreased linearly with increasing time. After 16 hours, infectious virus was no longer detectable.

EXAMPLE 4

The process described in Example 1 was carried out using an FMD virus solution of type $O_1$. After a reaction time of 4 hours, infectiousnes was no longer detectable.

EXAMPLE 5

FMD virus solutions of type C and type $O_1$ were each inactivated for 5 or 6 hours according to the process described in Example 1. Virus concentrates were prepared from the solutions with the aid of the known polyethylene glycol process and 5 receptive piglets were each inoculated intramuscularly with 1 ml of the concentrates. After no disease symptoms whatsoever showed over the course of 10 days, equal parts of the inactivated virus concentrates were mixed with an adjuvant and injected intramuscularly into 20 pigs. The animals all formed neutralizing antibodies against both active types of virus. Eight weeks after the vaccination, all 10 out of 10 animals were immune against infection with active FMD virus of type C, and 9 out of 10 animals were immune against infection with active FMD virus of type $O_1$; one animal fell ill, but substantially more mildly than the controls without pretreatment.

EXAMPLE 6

The process described in Example 1 was used for the inactivation of the virus of Infectious Bovine Rhinotracheitis (IBR) — an example of the viruses containing desoxyribonucleic acid — instead of FMD virus, which contains ribonucleic acid. Here again, a linear decrease in infectious strength was to be found, so that after 6 hours' reaction time, infectiousness was no longer detectable. Ten guinea pigs were each injected intramuscularly with 2 ml of a virus solution which had been treated for 6 hours. Three weeks after the vaccination, neutralizing antibodies against IBR virus were detectable in the serum of these animals.

EXAMPLE 7

Ethyleneimine, up to a final concentration of 0.05% (volume/volume), was added to a suspension of bacteria of *Pasteurella haemolitica* containing about $10^{10}$ bacteria/ml, in a manner analogous to the process described in Example 1. After 14 hours at 37° C, the bacterial mass was centrifuged off and re-suspended in sterile, phosphate-buffered sodium chloride solution.

A sample of the preparation thus obtained was inoculated into 3 different bacterial nutrient solutions and incubated at 37° C. Within 6 days, bacterial growth was no longer detectable.

A further sample thereof was injected intraperitoneally in doses of 0.1 ml into 20 mice. After 24 and 48 hours, the animals showed no disease symptoms, while out of 20 animals injected with the same, but untreated, bacterial suspension, 15 died within 16 hours and 5 within 24 hours.

A further sample thereof was mixed with an equal volume of an adjuvant. Five rabbits were each inoculated subcutaneously with 1.5 ml of this vaccine. The vaccination was repeated after 14 days. In none of these animals was bacteraemia observed. An antibody strength against the same bacterium was detectable in the serum of these animals with the aid of the agglutination test, and this strength rose noticeable after the booster inoculation.

What is claimed is:

1. A virus suspension to which ethyleneimine has been added such that the concentration of ethyleneimine is 0.005% to 2% V/V, the residual unused ethyleneimine thereafter being destroyed, whereby the virus is inactivated without impairment to its antigenicity or immunogenicity.

2. A virus suspension according to claim 1 wherein the addition of ethyleneimine is such that the concentration of ethyleneimine is 0.01% to 0.5% V/V.

3. A virus suspension according to claim 1 wherein the virus is FMD.

4. A virus suspension according to claim 3 wherein the virus is FMD, Types A, $O_1$ or C.

5. A virus suspension according to claim 1 wherein the virus is IBR.

6. A virus suspension according to claim 1 wherein the addition of ethyleneimine is such that the concentration of ethyleneimine is 0.03% V/V.

7. A virus suspension according to claim 1 wherein the addition of ethyleneimine is such that the concentration of ethyleneimine is 0.05% V/V.

8. A virus suspension according to claim 1 to which has been added a sufficient amount of sodium thiosulphate solution to destroy the residual unused ethyleneimine.

9. A virus suspension according to claim 1 to which has been added a sufficient amount of sodium sulphite solution to destroy the residual unused ethyleneimine.

10. A method of rendering virus inactive without impairing its antigenicity or immunogenicity which comprises adding to a virus a suspension of ethyleneimine such that the concentration of ethyleneimine in the suspension is 0.005% to 2% V/V, maintaining the temperature of the suspension between 0° C and 45° C for between a few hours and 2 days, and thereby destroying the residual unused ethyleneimine.

11. A method according to claim 10 wherein the addition of ethyleneimine is such that the concentration of ethyleneimine is 0.001% to 0.5% V/V.

12. A method according to claim 10 wherein the temperature is from 20° C to 37° C.

13. A method according to claim 10 wherein the virus is FMD.

14. A method according to claim 10 wherein the virus is FMD, Type A, $O_1$ or C.

15. A method according to claim 10 wherein the virus is IBR.

16. A method according to claim 14 wherein the addition of ethyleneimine is such that the concentration of ethyleneimine is 0.03% V/V.

17. A method according to claim 14 wherein the addition of ethyleneimine is such that the concentration of ethyleneimine is 0.5% V/V.

18. A method according to claim 15 wherein the addition of ethyleneimine is such that the concentration of ethyleneimine is 0.03% V/V.

19. A method according to claim 15 wherein the addition of ethyleneimine is such that the concentration of ethyleneimine is 0.05% V/V.

20. A method according to claim 10 wherein the residual unused ethyleneimine is destroyed by adding a sufficient amount of a sodium thiosulphate solution.

21. A method according to claim 10 wherein the residual unused ethyleneimine is destroyed by adding a sufficient amount of a sodium sulphite solution.

22. A method according to claim 10 wherein the residual unused ethyleneimine is destroyed by allowing the suspension to remain at a suitable temperature for a period of time sufficient to result in destruction of the excess ethyleneimine.

23. A pharmaceutical composition which comprises an amount of a virus suspension of claim 1 sufficient to be effective against the infection to be treated in combination with a pharmaceutically-acceptable, nontoxic, inert diluent or carrier.

24. A pharmaceutical composition according to claim 23 wherein the addition of ethyleneimine is such that the concentration of ethyleneimine is 0.01% to 0.5% V/V.

25. A pharmaceutical composition according to claim 23 wherein the virus is FMD.

26. A pharmaceutical composition according to claim 25 wherein the virus is FMD, Types A, $O_1$ or C.

27. A pharmaceutical composition according to claim 23 wherein the virus is IBR.

28. A pharmaceutical composition according to claim 23 wherein the addition of ethyleneimine is such that the concentration of ethyleneimine is 0.03% V/V.

29. A pharmaceutical composition according to claim 23 wherein the addition of ethyleneimine is such that the concentration of ethyleneimine is 0.05% V/V.

30. A pharmaceutical composition according to claim 23 wherein a sufficient amount of sodium thiosulphate solution has been added to the virus suspension to destroy the excess ethyleneimine.

31. A pharmaceutical composition according to claim 23 wherein a sufficient amount of sodium sulphite solution has been added to the virus suspension to destroy the excess ethyleneimine.

* * * * *